United States Patent [19]

Oxford et al.

[11] Patent Number: 4,795,756
[45] Date of Patent: Jan. 3, 1989

[54] 3-(2-AMINOETHYL)INDOLE DERIVATIVES

[75] Inventors: Alexander W. Oxford, Royston; Michael D. Dowle, Ware, both of England

[73] Assignee: Glaxo Group Limited, London, England

[21] Appl. No.: 30,625

[22] Filed: Mar. 27, 1987

[30] Foreign Application Priority Data

Mar. 27, 1986 [GB] United Kingdom ............... 8607824

[51] Int. Cl.$^4$ ............ A61K 31/40; C07D 209/16
[52] U.S. Cl. ............................ 514/415; 548/504; 564/157; 514/930
[58] Field of Search ............ 514/415; 548/504

[56] References Cited

U.S. PATENT DOCUMENTS 4,252,803  2/1981  Webb ............................ 544/80
4,650,810  3/1987  Bays et al. ...................... 514/415
4,672,067  6/1987  Coates et al. ................... 514/323

FOREIGN PATENT DOCUMENTS 2082175A  8/1981  United Kingdom .

OTHER PUBLICATIONS

Nishimura, Chem. Abs. 77, 165060x (1972).

Primary Examiner—Mark L. Berch
Attorney, Agent, or Firm—Bacon & Thomas

[57] ABSTRACT

Compounds are disclosed of formula (I)

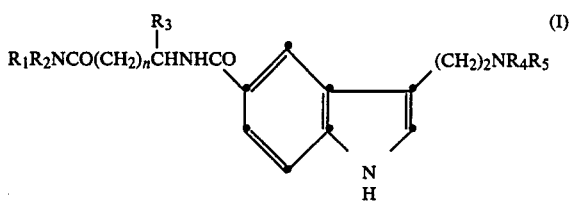

wherein
$R_1$ is H, $C_{1-6}$ alkyl, $C_{3-7}$ cycloalkyl, phenyl optionally substituted by $C_{1-3}$ alkoxy or phen($C_{1-4}$) alkyl in which the phenyl ring is optionally substituted by $C_{1-3}$ alkoxy;
$R_2$ is H or $C_{1-6}$ alkyl;
$R_3$ is H or $C_{1-3}$ alkyl;
$R_4$ and $R_5$ independently represents H, $C_{1-3}$ alkyl or 2-propenyl; and
n represents zero or 1;

and physiologically acceptable salts and solvates (e.g. hydrates) thereof.

The compounds have potent selective vasoconstrictor activity and are indicated as useful for the treatment of migraine. The compounds may be formulated as pharmaceutical compositions with physiologically acceptable carrier or excipients for administration by any convenient route. Various methods for the preparation of the compounds (I) are disclosed.

11 Claims, No Drawings

3-(2-AMINOETHYL)INDOLE DERIVATIVES

This invention relates to indole derivatives, to processes for their preparation, to pharmaceutical compositions containing them and to their medical use, in particular to compounds and compositions of use in the treatment of migraine.

The pain of migraine is associated with excessive dilatation of the cranial vasculature, and known treatments for migraine include the administration of compounds having vasoconstrictor properties, such as ergotamine. However, ergotamine is a non-selective vasoconstrictor which constricts blood vessels throughout the body and has undesirable and dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

A number of classes of compounds have been described having selective vasoconstrictor activity including, for example, the indole derivatives described in our UK Patent Specification No. 2082175 of formula:

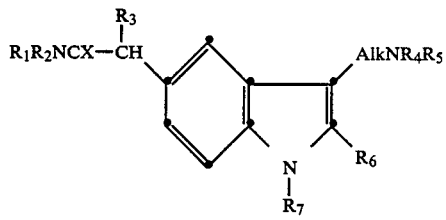

wherein $R_1$, $R_3$, $R_4$, and $R_6$ and $R_7$, which may be the same or different, each represents a hydrogen atom or an alkyl group;

$R_2$ represents a hydrogen atom or an alkyl, aryl, aralkyl, cycloalkyl or alkenyl group, or $R_1$ and $R_2$ together with the nitrogen atom to which they are attached form a saturated monocyclic 5 to 7-membered ring which may optionally contain a further heterofunction;

$R_5$ represents a hydrogen atom or an alkyl or alkenyl group, or $R_4$ and $R_5$ together form a aralkylidene group;

Alk represents an alkylene chain containing two or three carbon atoms which may be unsubstituted or substituted by not more than two $C_{1-3}$ alkyl groups;

X represents an oxygen or sulphur atom; and physiologically acceptable salts and solvates thereof.

As indicated in UK Patent Specification No. 2082175 compounds of the above formula selectively constrict the carotid arterial bed of the anaesthetised dog and are thus potentially useful for the treatment of migraine.

We have now found a novel group of indole derivatives having potent and selective vasoconstrictor activity.

Thus, the present invention provides an indole of the general formula (I):

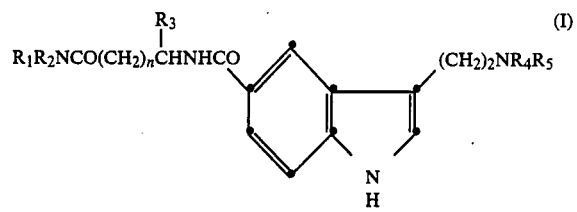

wherein
$R_1$ represents a hydrogen atom, a $C_{1-16}$ alkyl group, a $C_{3-7}$ cycloalkyl group, a phenyl group which may be unsubstituted or substituted by a $C_{1-3}$ alkoxy group or a phen($C_{1-4}$) alkyl group in which the phenyl ring may be unsubstituted or substituted by a $C_{1-3}$ alkoxy group;

$R_2$ represents a hydrogen atom or a $C_{1-6}$ alkyl group;

$R_3$ represents a hydrogen atom or a $C_{1-3}$ alkyl group;

$R_4$ and $R_5$ which may be the same or different each represents a hydrogen atom, a $C_{1-3}$ alkyl group or 2-propenyl; and n represents zero or 1; and physiologically acceptable salts and solvates (e.g. hydrates) thereof.

The invention includes within its scope all optical isomers of compounds of formula (I) and their mixtures, including the racemic mixtures thereof.

Referring to the general formula (I), the alkyl group may be straight chain or branched chain alkyl groups, such as methyl, ethyl or prop-2-yl groups. A cycloalkyl group represented by $R_1$ may be for example a cyclopentyl or cyclohexyl group.

When $R_1$ represents a substituted phenyl or substituted phen($C_{1-4}$)alkyl group the $C_{1-3}$ alkoxy substituent may be for example methoxy.

The alkyl moiety of the phen($C_{1-4}$)alkyl group may be for example a methyl or ethyl moiety.

A preferred class of compounds represented by the general formula (I) is that in which $R_1$ represents a hydrogen atom, a $C_{1-6}$ alkyl group, for example a methyl group, a phenyl group or a phen($C_{1-4}$)alkyl group, for example a phenylmethyl group.

In the compounds of formula (I), n is preferably zero.

Another preferred class of compounds of formula (I) is that wherein $R_2$ represents a hydrogen atom. A further preferred class of compounds is that in which $R_3$ represents a hydrogen atom.

Another preferred class of compounds of formula (I) is that in which $R_4$ and $R_5$, which may be the same or different each represents a hydrogen atom or a methyl group.

A still further preferred class of compounds falling within the scope of formula (I) is that wherein $R_1$ represents a hydrogen atom or a phenylmethyl group, $R_2$ and $R_3$ both represent a hydrogen atom, $R_4$ represents a hydrogen atom or a methyl group, $R_5$ represents a methyl group and n is zero.

Preferred compounds according to the invention include:
N-(2-Amino-2-oxoethyl)-3-[2-(methylamino)ethyl]-1H-indole-5-carboxamide;
N-(2-Amino-2-oxoethyl)-3-[2-(dimethylamino)ethyl]-1H-indole-5-carboxamide;
and physiologically acceptable salts and solvates thereof.

Suitable physiologically acceptable salts of the indoles of general formula (I) include acid addition salts formed with inorganic or organic acids, for example hydrochlorides, hydrobromides, sulphates, nitrates, phosphates, tartrates, citrates, fumarates, maleates, succinates, and sulphonates e.g. mesylates. Other salts may be useful in the preparation of compounds of formula (I) e.g. creatinine sulphate adducts.

It will be appreciated that the invention extends to other physiologically acceptable equivalents of the compounds according to the invention, i.e. physiologically acceptable compounds which are converted in vivo into the parent compound. Examples of such equivalents include physiologically acceptable, metabolically labile N-acyl derivatives.

Compounds of the invention selectively constrict the carotid arterial bed of the anaesthetised dog, whilst having a negligible effect on blood pressure. Their selective vasoconstrictor action has been demonstrated in vitro.

Compounds of the invention are useful in treating pain resulting from dilatation of the carotid vascular bed, in particular migraine and cluster headache.

Accordingly, the invention also provides a pharmaceutical composition adapted for use in human medicine which comprises at least one compound of formula (I) or a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may taken the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid). The liquid preparations may also contain conventional buffers, flavouring, colouring and sweetening agents as appropriate.

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, buccal or rectal administration to man (of average bodyweight e.g. about 70 kg) for the treatment of migraine is 0.1 to 100 mg of the active ingredient per unit dose which could be administered, for example, 1 to 4 times per day. It will be appreciated that it may be necessary to make routine variations to the dosage depending on the age and weight of the patient as well as the severity of the condition to be treated. The dosage will also depend on the route of administration.

For oral administration a unit dose will preferably contain from 2 to 50 mg of the active ingredient. A unit dose for parenteral administration will preferably contain 0.2 to 5 mg of the active ingredient.

Aerosol formulations are preferably arranged so that each metered does or 'puff' delivered from a pressurised aerosol contains 0.2 to 2 mg of a compound of the invention and, each dose administered via capsules or cartridges in an inhaler or insufflator contains 0.2 to 20 mg. The overall daily dose by inhalation will be within the range 1 mg to 100 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of formula (I), and physiologically acceptable salts or solvates (e.g. hydrates) thereof, may be prepared by the general methods outlined below. In the following processes, $R_1$, $R_2$, $R_3$, $R_4$, $R_5$ and n are as defined for the general formula (I) unless otherwise specified.

According to one general process (A), a compound of general formula (I) may be prepared by reacting an acid of general formula (II):

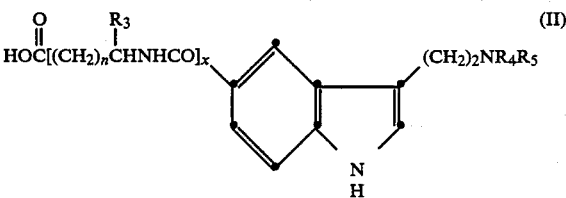

(wherein) x is zero or 1) or an acylating derivative thereof (e.g. an acid halide, anhydride or an ester), or a salt (for example an organic or inorganic acid addition salt such as the hydrochloride, hydrobromide, sulphate or maleate salt, or creatinine sulphate adduct) or a protected derivative thereof, with an appropriate amine of general formula (III):

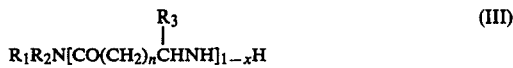

$$R_1R_2N[CO(CH_2)_nCHNH]_{1-x}H \quad \overset{R_3}{|} \quad (III)$$

or a salt (e.g. hydrochloride) thereof.

The above reaction is preferably effected using an activated derivative of formula (II).

Activated derivatives of general formula (II) which may be employed in the preparation of compounds of formula (I) include acid anhydrides (e.g. mixed anhydrides such as pivalic anhydride or diphenyl carbamic anhydride or formed with a sulphonyl halide such as methanesulphonyl chloride, or a haloformate such as a lower alkylhaloformate); esters (e.g. methyl, ethyl,p-nitrophenyl or 1-methlpyridinium ester); and acid halides (e.g. acid chlorides).

When using an activated derivative of general formula (II) the condensation process may be effected in aqueous or non-aqueous reaction media and conveniently at a temperature of from $-70°$ to $+150°$ C. Thus the condensation reaction using an alkyl ester may be effected in a suitable reaction medium such as an alcohol e.g. methanol; an amide e.g. dimethylformamide; an ether e.g. tetrahydrofuran or diethylether; or mixtures thereof and conveniently at a temperature of from 0° to 100° C. The condensation reaction using an acid halide, anhydride or activated ester may be effected in a suitable reaction medium such as an amide e.g. N,N-dimethylformamide; an ether e.g. tetrahydrofuran or diethylether; a nitrile e.g. acetonitrile; a halogenated hydrocarbon e.g. dichloromethane; or mixtures thereof preferably at a temperature of from $-5°$ to $+30°$ C. The condensation reaction may if desired be carried out in the presence of a base, such as a tertiary amine (e.g. triethylamine or pyridine); or an inorganic base such as an alkali metal carbonate (e.g. potassium carbonate) or bicarbonate (e.g. sodium bicarbonate). A tertiary amine base such as pyridine may also act as the reaction solvent. In some instances, for example when x is 1, the amine of general formula (III) may itself act as the reaction solvent.

If desired, the above condensation reactions may be carried out in the presence of a catalyst such as 4-dimethylaminopyridine.

When an acid of general formula (II) is employed, the reaction is desirable conducted in the presence of a coupling agent, for example N,N'- carbonyldiimidazole or a carbodiimide such as N,N'-dicyclohexyl-carbodiimide. The condensation reaction may be carried out in a suitable reaction medium preferably an anhydrous medium, conveniently at a temperature of from $-50°$ to $+50°$ C., preferably $-5°$ to $+30°$ C. Suitable solvents include halogenated hydrocarbons e.g. dichloromethane; nitriles e.g. acetonitrile; amides e.g. N,N-dimethylformamide; and ethers e.g. tetrahydrofuran; as well as mixtures of two or more such solvents. The reactiion may also be carried out in the absence of a coupling agent in a suitable reaction medium such as a hydrocarbon (e.g. toluene or xylene) conveniently at a temperature of from 50° to 120° C.

Where it is desired to prepare a compound of formula (I) in which $R_1$ and $R_2$ are both hydrogen atoms the condensation may be effected using ammonia, which may be for example be employed in the form of aqueous ammonia or in a solvent such as methanol.

Acids and activated derivatives of formula (II) wherein x is zero may be prepared as described for example in UK Published Patent Application No. 2035310. Compounds of formula (II) wherein x is 1 may be prepared by analogous methods. Activated derivatives of general formula (II) wherein x is 1 may also be prepared by reacting an activated derivative of formula (II) wherein x is zero with an amino acid ester of formula R'CO(CH$_2$)$_n$CH(R$_3$)NH$_2$, (wherein R' represents an alkoxy group, preferably a C$_{1-6}$ alkoxy group) or a salt (e.g. a hydrochloride) thereof, as described for general process (A) itself.

The intermediate compounds of general formula (II) wherein x is 1 and the acylating derivatives thereof, are novel compounds and constitute a further feature of this invention.

According to another general process (B), compounds of formula (I) may be prepared by the cyclisation of a compound of general formula (IV):

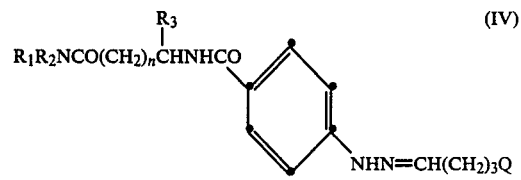

$$R_1R_2NCO(CH_2)_n\overset{R_3}{\underset{|}{C}}HNHCO \quad (IV)$$

wherein Q is the group NR$_4$R$_5$ (or a protected derivative thereof) or a leaving atom or group such as a halogen atom (e.g. chlorine or bromine) or an acyloxy group (e.g. a carboxylic or sulphonic acyloxy group such as an acetoxy, chloroacetoxy, dichloroacetoxy, trifluoroacetoxy, p-nitrobenzoyloxy, p-toluenesulphonyloxy or methanesculphonyloxy group).

The reaction may conveniently be effected in aqueous or non-aqueous reaction media, and at temperature of from 20° to 200° C., preferably 50° to 125° C.

Particularly convenient embodiments of the process are described below.

When Q is the group NR$_4$R$_5$ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.g. methanol, ethanol or isopropanol) or as aqueous ether (e.g. dioxan or tetrahydrofuran) as well as mixtures of such solvents and the acid catalyst may be, for example, an inorganic acid such as concentrated hydrochloric or sulphuric acid. (In some cases the acid catalyst may also act as the reaction solvent). In an anhydrous reaction medium, which may comprise one or more alcohols or ethers (e.g. as previously described) or esters (e.g. ethyl acetate), the acid catalyst will generally be a Lewis acid such as boron trifluoride, zinc chloride or magnesium chloride.

When Q is a leaving atom or group such as a chlorine or bromine atom the reaction may be effected in an aqueous organic solvent, such as an aqueous alcohol (e.g. methanol, ethanol or isopropanol) or an aqueous ether (e.g. dioxan or tetrahydrofuran) in the absence of an acid catalyst, conveniently at a temperature of from 20° to 200° C., preferably 50° to 125° C. This process results in the formation of a compound of formula (I) wherein $R_4$ and $R_5$ are both hydrogen atoms.

According to a particular embodiment of general process (B) compounds of formula (I) may be prepared directly by the reaction of a compound of general formula (V):

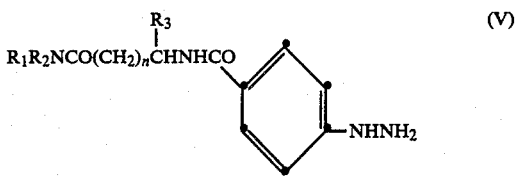

or a salt thereof,
with a compund of formula (VI):

$$OHC(CH_2)_3Q \qquad (VI)$$

(wherein Q is as defined above) or a salt or protected derivative thereof (such as an acetal or ketal e.g. formed with an appropriate alkyl orthoformate or diol, or protected as a bisulphite addition complex) using the appropriate conditions as described above for the cyclisation of compounds of general formula (IV). It will be appreciated that in this embodiment of the cyclisation process (B) a compound of general formula (IV) is formed as an intermediate, and may either be isolated prior to cyclisation or reacted in situ to form the desired compound of general formula (I).

Compounds of general formula (IV) may, if desired, be isolated as intermediates during the process for the preparation of compounds of formula (I) wherein a compound of formula (V), or a salt or protected derivative thereof, is reacted with a compound of formula (VI), or a salt or protected derivative thereof, in a suitable solvent, such as an aqueous alcohol (e.g. methanol) at a temperature of, for example, 20° to 30° C. If an acetal or ketal of a compound of formula (VI) is used, it may be necessary to carry out the reaction in the presence of an acid (for example, acetic or hydrochloric acid).

Compounds of general formula (V) may be prepared for example from the corresponding nitro compounds, using conventional procedures.

A further general process (C) for preparing compounds of general formula (I) involves reacting a compound of general formula (VII):

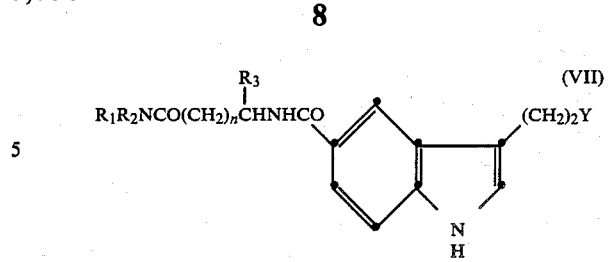

(wherein Y is a readily displaceable atom or group) or a protected derivative thereof, with an amine of formula $R_4R_5NH$.

The displacement reaction may conveniently be carried out on those compounds of formula (VII) wherein Y is a halogen atom (e.g. chlorine, bromine or iodine) or a group $OR_6$ where $OR_6$ is, for example, an acyloxy group which may be derived from a carboxylic or sulphonic acid, such as an acetoxy, chloroacetoxy, dichloroacetoxy, trifluoroacetoxy, p-nitrobenzoyloxy, p-toluenesulphonyloxy or methanesulphonyloxy group.

The displacement reaction may be conveniently effected in an inert organic solvent (optionally in the presence of water), examples of which include alcohols, e.g. ethanol; cyclic ethers, e.g. dioxan or tetrahydrofuran; acylic ethers e.g. diethylether; esters, e.g. ethyl acetate; amides, e.g. N,N-dimethylformamide; and ketones e.g. acetone or methylethyl ketone, at a temperature of from $-10°$ to $+150°$ C., preferably 20° to 50° C.

The compounds of general formula (VII) wherein Y is a halogen atom may be prepared by reacting a hydrazine of general formula (V) with an aldehyde or ketone (or a protected derivative thereof) of formula (VI) in which Q is a halogen atom, in an aqueous alkanol (e.g. methanol) containing an acid (e.g. acetic or hydrochloric acid). Compounds of formula (VII) wherein Y is the group $OR_6$ may be prepared from the corresponding compound wherein Y is a hydroxyl group by acylation with the appropriate activated species (e.g. anhydride or sulphonyl chloride) using conventional techniques. The intermediate alcohol may be prepared by cyclisation of a compound of formula (IV) wherein Q is a hydroxyl group (or a protected derivative thereof) under standard conditions.

Compounds of formula (I) may also be prepared by another general process (D) involving reduction of a compound of general formula (VIII):

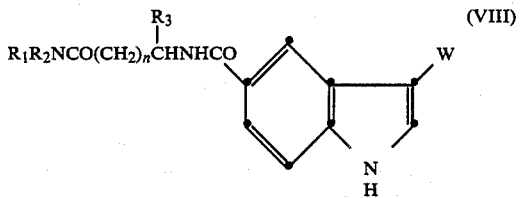

(wherein W is a group capable of being reduced to give the required $-(CH_2)_2NR_4R_5$ group or to give a protected derivative of the $-(CH_2)_2NR_4R_5$ group) or a salt or protected derivative thereof.

The required $-(CH_2)_2-$ and $-NR_4R_5$ groups may be formed by reduction steps which take place separately or together in any appropriate manner.

Groups which may be reduced to the $-(CH_2)_2-$ moiety include the the corresponding unsaturated group and corresponding groups containing one or more carbonyl functions and/or a hydroxyl group.

Groups which may be reduced to the group —$NR_4R_5$ where $R_4$ and $R_5$ are both hydrogen include nitro, azido, hydroxyimino and nitrile groups. In the latter case, reduction yields the group —$CH_2NH_2$ and thus provides a methylene group of the —$(CH_2)_2$— moiety.

The required —$NR_4R_5$ group wherein $R_4$ and/or $R_5$ other than hydrogen may be prepared by reduction of a nitrile —$CH_2CN$ or an aldehyde —$CH_2CHO$ in the presence of an amine, $R_4R_5NH$.

A particularly suitable method for preparing a compound of formula (I) wherein $R_4$ and/or $R_5$ is other than hydrogen is reductive alkylation of the corresponding compound wherein $R_4$ and/or $R_5$ represent hydrogen with an appropriate aldehyde or ketone (e.g. formaldehyde or acetone) in the presence of a suitable reducing agent. In some instances (e.g. for the introduction of the group(s) $R_4$ and/or $R_5$, where these represent methyl) the aldehyde (e.g. formaldehyde) may be condensed with the amine and the intermediate thus formed may subsequently be reduced using a suitable reducing agent.

Examples of groups represented by the substituent W thus include —$(CH_2)_2NO_2$; —$CH=CHNO_2$; —$(CH_2)_2N_3$; —$CH_2CN$; —$CH_2CHO$; —$COCH_2Z$; —$CH_2CH=NOH$; and —$CH(OH)CH_2NR_4R_5$ (wherein Z is an azido group or the group —$NR_4R_5$ or a protected derivative thereof).

The reduction according to general process (D) may be effected by conventional methods, for example, by catalytic hydrogenation or using a reducing agent such as an alkali metal or alkaline earth metal borohydride or cyanoborohydride, or a metal hydride. The reduction may conveniently be effected in an organic reaction medium, which may comprise one or more solvents and at temperatures between $-20°$ and $+150°$ C. Suitable solvents include alcohols e.g. ethanol or propanol; cyclic ethers e.g. dioxan or tetrahydrofuran; acyclic ethers e.g. diethylether; amides e.g. dimethylformamide; esters e.g. ethyl acetate; and nitriles e.g. acetonitrile.

It will be appreciated that the choice of reducing agent and reaction conditions will be dependent on the nature of the group W, and other groups already present on the molecule.

Suitable reducing agents which may be used in the above process for the reduction of compounds of formula (VIII) wherein W represents, for example, the groups —$(CH_2)_2NO_2$, —$CH=CHNO_2$, —$(CH_2)_2N_3$, —$CH_2CN$, —$CH_2CH=NOH$ and —$CH(OH)CH_2NR_4R_5$ include hydrogen in the presence of a metal catalyst, for example Raney Nickel or a noble metal catalyst such as platinum, platinum oxide, palladium, palladium oxide or rhodium, which may be supported, for example, on charcoal, kieselguhr or alumina. In the case of Raney Nickel, hydrazine may also be used as the source of hydrogen. This process may conveniently be carried out in a solvent such as an alcohol e.g. ethanol; an ether, e.g. dioxan or tetrahydrofuran, an amide, e.g. dimethylformamide; or an ester e.g. ethyl acetate, and at a temperature of from $-10°$ to $+50°$ C., preferably $-5°$ to $+30°$ C.

The reduction process may also be effected on compounds of formula (VIII) wherein W represents, for example, the groups —$(CH_2)_2NO_2$, —$CH=CHNO_2$, —$(CH_2)_2N_3$, —$CH(OH)CH_2NR_4R_5$ or —$COCH_2Z$ (where Z is as previously defined), using an alkali metal or alkaline earth metal borohydride or cyanoborohydride e.g. sodium or calcium borohydride or cyanoborohydride which process may conveniently be carried out in an alcohol such as propanol or ethanol, or a nitrile such as acetonitrile, and at a temperature of from $10°$ to $100°$ C., preferably $50°$ to $100°$ C. In some instances the reduction using a borohydride may be carried out in the presence of cobaltous chloride.

Reductive alkylation of a compound of formula (VIII) may be effected using an alkali earth metal borohydride or cyanoborohydride. The reaction may be effected in an aqueous or non-aqueous reaction medium, conveniently in an alcohol (e.g. methanol or ethanol) or an ether (e.g. dioxan or tetrahydrofuran) optionally in the presence of water. The reaction may conveniently be carried out at a temperature in the range $0°$ to $100°$ C., preferably $5°$ to $50°$ C.

A particular embodiment of general process (D) is the reduction of a compound of formula (VIII) wherein W is the group —$CH_2CN$, for example by catalytic reduction with hydrogen in the presence of a catalyst such as palladium on charcoal or rhodium on alumina, optionally in the presence of an amine $HNR_4R_5$. The reduction may be effected in a suitable solvent such as an alcohol, e.g. methanol or ethanol.

A compound of general formula (I) where $R_5$ is a hydrogen atom may also be prepared by reduction of a corresponding compound wherein $R_5$ is a benzyl group, e.g. with hydrogen in the presence of a catalyst, e.g. 10% palladium on carbon.

The starting materials or intermediate compounds of formula (VIII) wherein W represents —$(CH_2)_2NO_2$, —$CH=CHNO_2$, —$CH_2CN$ or —$COCH_2Z$ may be prepared by analogous methods to those described in UK Published Patent Application No. 2035310, and 'A Chemistry of Heterocyclic Compounds—Indoles Part II', Chapter VI, edited by W J Houlihan (1972) Wiley Interscience, New York.

Compounds of formula (VIII), wherein W is the group —$CH_2CHO$ may be prepared by oxidation (e.g. with Jones' reagent) of a compound of formula (VII) wherein Y is a hydroxyl group. A compound of formula (VIII) wherein W is the group —$CH_2CH=NOH$ may be prepared by treatment of the corresponding aldehyde with hydroxylamine hydrochloride using standard conditions.

The intermediate compound of formula (VIII) wherein W is the group —$(CH_2)_2N_3$ may be prepared from a compound of formula (VIII) wherein Y is a halogen atom using standard procedures.

Standard reducing agents such as sodium borohydride may be used to prepare a compound of formula (VII) wherein W is the group —$CH(OH)CH_2NR_4R_5$ from the corresponding compound of formula (VIII) wherein W is the group —$COCH_2NR_4R_5$.

According to a further general process (E) a compound of formula (I) according to the invention, or a salt or protected derivative thereof, may be converted into another compound of formula (I) using conventional procedures.

For example, a compound of general formula (I) wherein one or more of $R_1$, $R_2$, $R_4$ and $R_5$ are alkyl groups may be prepared from the corresponding compounds of formula (I) wherein one or more of $R_1$, $R_2$, $R_4$ and $R_5$ represent hydrogen atoms, by reduction with a suitable alkylating agent such as a compound of formula $R_xL$, (where $R_x$ represents the desired $R_1$, $R_2$, $R_4$ or $R_5$ group and L represents a leaving atom or group such as a halogen atom or a tosylate group) or a sulphate $(R_x)_2SO_4$. Thus, the alkylating agent may be for example an alkyl halide (e.g. methyl or ethyl iodide), alkyl tosylate (e.g. methyl tosylate) or dialkylsulphate (e.g. dimethylsulphate).

The alkylation reaction may conveniently be carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides such as sodium or potassium hydride; alkali metal amides such as sodium amide; alkali metal carbonates such as sodium carbonate; alkali metal alkoxides such as sodium or potassium methoxide, ethoxide or t-butoxide; and tetrabutylammonium fluoride. When an alkyl halide is employed as the alkylating agent the reaction may also be carried out in the presence of an acid scavenging agent such as propylene or ethylene oxide. The reaction may be conveniently effected at a temperature of from $-20°$ to $+100°$ C.

Compounds of formula (I) wherein $R_1$ representss a cycloalkyl or phenylalkyl group and/or one or both of $R_4$ and $R_5$ represents propenyl may be prepared similarly, using an appropriate compound of formula $R_xL$ or $(R_x)_2SO_4$.

According to another general process (F), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_4R_5$, wherein $R_4$ and/or $R_5$ represents hydrogen, by protonation or with a group easily removable at the end of the reaction sequence. Such groups may include, for example, aralkyl groups, such as benzyl, diphenylmethyl or triphenylmethyl; or acyl groups such as N-benzyloxycarbonyl, t-butoxycarbonyl or phthaloyl.

In some cases, it may also be desirable to protect the indole nitrogen with, for example, an aralkyl group such as benzyl.

Subsequent cleavage of the protecting group or groups may be achieved by conventional procedures. Thus an aralkyl group such as benzyl, may be cleaved by hydrogenolysis in the presence of a catalyst (e.g. palladium on charcoal) or sodium and liquid ammonia; an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (E) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (E).

Thus, according to a further aspect of the invention, the following reactions in any appropriate sequence may if necessary and/or desired by carried out subsequent to any of the processes (A) to (E):

(i) removal of any protecting groups; and (ii) conversion of a compound of general formula (I) or a salt thereof into a physiologically acceptable salt or solvate (e.g. hydrate) thereof.

Where it is desired to isolate a compound of the invention as a salt, for example as an acid addition salt, this may be achieved by treating the free base of general formula (I), with an appropriate acid, preferably with an equivalent amount, or with creatinine sulphate in a suitable solvent (e.g. aqueous ethanol).

The starting materials or intermediate compounds for the preparation of the compounds according to this invention may be prepared by analogous methods to those described in UK Published Patent Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced before or after cyclisation to form the indole nucleus. It should therefore be appreciated that in such multi-stage processes, the sequences of reactions should be chosen in order that the reaction conditions do not affect groups present in the molecule which are desired in the final product.

The invention is further illustrated by the following Examples. All temperatures are in ° C.

Chromatography was carried out either in the conventional manner using silica gel (Merck, Kieselgel 60, Art. 7734) or by flash chromatography on silica (Merck 9385) and thin layer chromatography (t.l.c.) on silica (Macherly-Nagel, Polygram) except where otherwise stated.

Intermediates were routinely checked for purity by t.l.c. employing u.v. light for detection and spray reagents such as potassium permanganate (KMnO$_4$). In addition indolic intermediates were detected by spraying with aqueous ceric sulphate (CeIV) and tryptamines by spraying with a solution of iodoplatinic acid (IPA) or ceric sulphate.

The following abbreviations define the eluents used for column chromatography and t.l.c.:

| | |
|---|---|
| (A) Ethyl acetate-isopropanol-water-0.88 ammonia | 25:15:8:2 |
| (B) Chloroform-methanol | 19:1 |
| (C) Methylene chloride-ethanol-0.88 ammonia | 50:8:1 |
| (D) Methylene chloride-ethanol-0.88 ammonia | 25:8:1 |

Proton ($^1$H) nuclear magnetic resonance (n.m.r.) spectra were obtained either at 90 MHz using a Varian EM 390 instrument or at 250 MHz using a Bruker AM or WM 250 instrument. s=singlet, d=doublet, t=triplet, m=multiplet and q=quartet.

INTERMEDIATE 1

Methyl 3-[(dimethylamino)methyl]-1H-indole-5-carboxylate hydrochloride

A solution of methyl 1H-indole-5-carboxylate (0.24 g) in dry acetonitrile (15 ml) containing N,N-dimethyl)methylene)ammonium chloride (0.13 g) was stirred at room temperature, under nitrogen, for 5 h. The resulting precipitate was filtered off, and dried in vacuo at room temperature overnight to give the *title compound* as a solid (0.3 g) m.p. 197°–199°.

INTERMEDIATE 2

Methyl 3-(cyanomethyl)-1H-indole-5-carboxylate

Methyl iodide (2.3 ml) was added portionwise to a stirred solution of Intermediate 1, as the free base (7.8 g) in dry dimethylsulphoxide (50 ml). The resulting suspension was stirred at room temperature for 30 min, potassium cyanide (11.0 g) added, and the suspension stirred at room temperature for 18 h. The suspension was then partitioned between water (500 ml) and ethyl acetate (2×200 ml). The combined extracts were washed with water (200 ml) dired (MgSO$_4$) and evaporated in vacuo. The residue was purified by 'flash' chromatography (B) to give a solid (2.4 g). A sample (0.5 g) was crystallised from a mixture of ethyl acetate and hexane to give the *title compound* as a solid (0.35 l g) m.p. 127°–129°.

INTERMEDIATE 3

3-(Cyanomethyl)-1H-indole-5-carboxylic acid

A suspension of Intermediate 2 (1.8 g) in a mixture of methanol (30 ml) and sodium hydroxide (2N, 15 ml) was stirred at room temperature for 3 days. The methanol was evaporated in vacuo, and the residue partitioned between hydrochloric acid (2N, 50 ml) and ethyl acetate (2×50 ml). The combined extracts were dried (MgSO$_4$) and evaporated in vacuo to give a solid which was crystallised from ethyl acetate to give the *title compound* as a solid. (1.0 g) m.p. 248°–250° (decomp.)

INTERMEDIATE 4

3-[2-(Dimethylamino)ethyl]-1H-indole-5-carboxylic acid hydrochloride

A suspension of 10% palladised charcoal (0.4 g) in ethanol (10 ml) was stirred under an atmosphere of hydrogen until uptake ceased. To the catalyst was added a solution of Intermediate 3 (0.45 g) in 33% ethanolic dimethylamine (20 ml) and the mixture was again stirred under an atmosphere of hydrogen until all the starting material had been consumed. The suspension was filtered and the filtrate was evaporated under reduced pressure. The residue was dissolved in ethanol (10 ml) and the solution was treated with ethanolic hydrogen chloride until it was just acidic. Evaporation of the solvent gave a gum which crystallised from propan-2-ol (15 ml) as a powder (0.35 g), m.p. 200–1°. An analytical sample crystallised from ethanol had m.p. 205–6°.

EXAMPLE 1

N-(2-Amino-2-oxoethyl)-3-(2-aminoethyl)-1H-indole-5-carboxamide hydrochloride compound with ethanol and water, 5:5:1:1

(i) Phenylmethyl 2-[5-[[(2-amino-2-oxoethyl)amino]carbonyl]-1H-indol-3-yl]ethyl carbamate A mixture of phenylmethyl 2-[5-[[[(diphenylamino)-carbonyl]oxo]-carbonyl]-1H-indol-3-yl]ethyl carbamate (Intermediate 5, prepared as in British Specification No. 2035310) (4.0 g), glycinamide hydrochloride (1.1 g) and sodium acetate (1.4 g) in dimethylformamide (50 ml) was stirred for 3 h at room temperature. The solution was then partitioned between saturated sodium chloride (200 ml) and ethyl acetate (200 ml), and the aqueous phase further extracted with ethyl acetate (100 ml). The combined organic extracts were washed with water (3×100 ml), and dried (MgSO$_4$). Removal of the solvent gave a solid (3.2 g). Chromatography on silica gel, eluting with 0–5% methanol in chloroform, afforded a solid (1.5 g) which was recrystallised from aqueous ethanol to give the *title compound* as a crytalline solid, m.p. 185°–186° (0.75 g).

(ii) N-(2-Amino-2-oxoethyl)-3-(2-aminoethyl)-1H-indole-5-carboxamide hydrochloride compound with ethanol and water (5:5:1:1)

The product of Stage (i) (0.55 g) in ethanol (90 ml) was hydrogenated over palladium oxide on charcoal (5%, 0.24 g) for 3 h at room temperature and atmospheric pressure. The catalyst was removed by filtration and washed with ethanol (2×30 ml). The filtrates were combined and concentrated to a clear glass, which was taken up in ethanol (2 ml), treated with ethereal hydrogen chloride (6 ml) and diluted with ether (30 ml). The solid that formed was washed with ether (2×20 ml) and dried at 60°/0.4 torr. for 18 h to give the *title compound* as an amorphous solid m.p. 170°–185° (0.34 g).

Analysis found : C, 51.9; H, 6.0; N, 18.0. C$_{13}$H$_{16}$N$_4$O$_2$.HCl 0.2C$_2$H$_5$OH 0.2H$_2$O requires : C, 52.0; H, 6.0; N, 18.1%.

N.m.r. δ(DMSO-d6) includes 3.00 (4H, br s, CH$_2$CH$_2$N), 3.90 (2H, d, N—CH$_2$—C═O), 7.07 (1H, s, CONH$_2$ (one)), 8.75 (1H, br t, CONH-CH$_2$) and 11.3 (1H, br s, indole —NH).

EXAMPLE 2

N-[2-(Methylamino)-2-oxoethyl]-3-(2-aminoethyl)-1Hindole-5-carboxamide hydrochloride compound with ethanol and water 10:10:3:3

(i) Methyl [[[3-[2-[[(phenylmethoxy)carbonyl]amino]ethyl]-1H-indol-5-yl]carbonyl]amino]acetate Intermediate 5 (3.3 g), methyl glycinate hydrochloride (1.55 g) and sodium acetate (1.23 g) were stirred together at room temperature in dimethylformamide for 1 h. The mixture was partitioned in dimethylformamide for 1 h. The mixture was partitioned between ethyl acetate (150 ml) and water (150 ml), and the aqueous layer further extracted with ethyl acetate (150 ml). The combined organic extracts were washed with water (2×100 ml), and dried (Na$_2$SO$_4$). The solvent was evaporated in vacuo to give an oil (4.1 g) which was chromatographed on silica using a nmixture of 0–2% methanol in chloroform as eluent. The appropriate fractions were calculated, and the solvent was evaporated in vacuo to give a solid (2.0 g). Recrystallisation from isopropyl acetate gave the *title compound* (1.5 g) as microcrystals m.p. 118°–119°.

(ii) Phenylmethyl 2-[5-[[[2-(methylamino)-2-oxoethyl]amino]carbonyl]-1H-indol-3-yl]ethyl carbamate The product of Stage (i) (1.0 g) was stirred in 33% solution of methylamine in ethanol (5 ml) at room temperature for 5 min. The solvent was evaporated in vacuo and the solid was triturated with hot ethyl acetate. The product was filtered off and dried in vacuo to give the *title compound* (0.96 g), m.p. 178°–180°.

(iii)
N-[2-(methylamino)-2-oxoethyl]-3-(2-aminoethyl)-1H-indole-5-carboxamide hydrochloride compound with ethanol and water 10:10:3:3

A solution of the product of Stage (i) (0.95 g) in ethanol (120 ml) was hydrogenated over 10% palladium on charcoal (0.4 g) for 1 h. The catalyst was filtered off, and washed with ethanol (50 ml). The filtrate was evaporated in vacuo to give a clear glass, which was dissolved in ethanol (5 ml), and ethereal hydrogen chloride (2 ml) was added. The mixture was diluted with dry ether (80 ml), and the resultant solid was filtered off. The solid was washed with ether (2 ×15 ml) and dried at 60° C./0.4 torr for 16 h to give the title compound (0.66 g), m.p. 110°–120°.

Analysis found : C,53.5; H,6.2; N,16.8; $C_{14}H_{18}N_4O_2 \cdot HCl \cdot 0.3C_2H_6O \cdot 0.3H_2O$ requires : C,53.1; H,6.5; N,17.0%

N.m.r. δ(DMSO-d6) includes 2.65 (3H, d, $CH_3$—NH), 3.0 (4H, br s, $CH_2CH_2N$) 3.90 (2H, d, $CH_2$—NH—C=O) 8.70 (1H, br t, $CH_2$—NH—C=O) and 11.3 (1H, br s, indole —NH).

EXAMPLE 3
N-(2-Amino-2-oxo-1-methylethyl)-3-(2-aminoethyl)-1H-indole 5-carboxamide hydrochloride compound with ethanol and water (10:10:4:1)

(i) Ethyl 2-[[[3-[2-[[(phenylmethoxy)carbonyl]amino]ethyl]-1H-indol-5-yl]carbonyl]amino]propanoate Intermediate 5 (6.0 g), D,L-alanine ethyl ester (3.8 g) and potassium carbonate (3.5 g) were stirred together in dimethylformamide (30 ml) at room temperature for 4 h. The mixture was partitioned between ethyl acetate (150 ml) and water (150 ml), and the aqueous phase further extracted with ethyl acetate (150 ml). The organic extracts were combined and washed with water (2×100 ml). The organic phase was dried ($Na_2SO_4$) and the solvent evaporated in vacuo to give a solid which was chromatographed on silica using ethyl acetate as eluent. The appropriate fractions were combined, and the solvent evaporated in vacuo to give a solid. Recrystallisation from isopropyl acetate gave the *title compound* as a microcrystalline solid (2.5 g), m.p. 143°–144°.

(ii) Phenylmethyl 2-[5-[[[2-(1-amino-1-oxo)propyl]amino]carbonyl]-1H-indol-3-yl]ethyl carbamate The product of Stage (i) (1.0 g) was stirred in a mixture of aqueous ammonia (0.88, 60 ml) and methanol (80 ml) for 16 h. The mixture was partitioned between ethyl acetate (100 ml) and hydrochloric acid (150 ml). The organic layer was separated, dried ($Na_2SO_4$) and the solvent was evaporated in vacuo to give a semi-solid (1.1 g), which was chromatographed on silica (50 g) using ethyl acetate as eluent. The appropriate fractions were combined, and the solvent was evaporated in vacuo to give a colourless glass (0.7 g). The *title compound* crystallised from ethyl acetate as a solid (0.5 g), m.p. 163°–165°.

(iii)
N-(2-Amino-2-oxo-1-methylethyl)-3-(2-aminoethyl)-1H-indole-5-carboxamide hydrochloride compound with ethanol and water (10:10:4:1)

A solution of the product of Stage (ii) (0.35 g) in ethanol (50 ml) was hydrogenated over 10% palladium on carbon (0.2 g) at room temperature and atmospheric pressure for 2 h. The catalyst was filtered off, and washed with ethanol (2×20 ml). The combined filtrates were evaporated in vacuo to give a clear glass (0.21 g) which was dissolved in ethanol (4 ml) and treated with ethereal hydrogen chloride (1 ml). The mixture was diluted with dry ether (100 ml) and stirred for 10 min. The resulting solid was filtered off, washed with ether (2×20 ml) and dried at 60° C./0.4 torr for 4 h to give the *title compound* as a solid (0.18 g), m.p. 135°–145°.

Analysis found : C,53.6; H,6.4; N,16.7; $C_{14}H_{18}N_4O_2 \cdot HCl \cdot 0.4C_2H_6O \cdot 0.1H_2O$ requires : C,53.7; H,6.6; N,16.9%.

N.m.r δ(DMSO-d6) includes 1.40 (3H, d, $CH_3$-CH), 3.05 (4H, br s, $CH_2CH_2N$) 4.55 (1H, qui, $CH_3$-$CH$) and 11.4 (1H, br s, indole —NH).

EXAMPLE 4
N-(2-Amino-2-oxoethyl)-3-[2-(methylamino)ethyl]-1H-indole-5-carboxamide hydrochloride compound with ethanol and water (10:10:1:3)

(i)
N-(2-Amino-2-oxoethyl)-3-[2-(phenylmethylamino)ethyl]-1H-indole-5-carboxamide hydrochloride compound with ethanol (5:5:1)

The product of Example 1 (as the free base) (1.3 g) and benzaldehyde (0.53 g) were dissolved in absolute ethanol (20 ml) and stirred at room temperature for 20 h. Sodium borohydride (0.19 g) was then added in portions over 10 min. The solution was stirred for an additional 15 min, and the solvent was evaporated in vacuo. The residue was dissolved in dilute hydrochloric acid, and the solution basified with sodium hydrogen carbonate (2N, 40 ml). The solution was saturated with potassium carbonate, and extracted with ethyl acetate (7 ×50 ml). The organic extracts were combined, dried ($Na_2SO_4$) and the solvent evaporated in vacuo to give a glass (1.67 g). A small portion of this product (0.25 g) was dissolved in ethanol (3 ml), and ethereal hydrogen chloride (1 ml) was added. The mixture was diluted with ether (40 ml), and the resulting solid was filtered, washed with ether (2×30 ml), and dried at 60° C./0.5 torr for 16 h to give the title compound (0.14 g) m.p. 105°–120°.

Analysis found : C,61.9; H,6.2; N,14.2; $C_{20}H_{22}N_4O_2 \cdot HCl \cdot 0.2C_2H_6O$ requires : C,61.9; H,6.2; N,14.2%.

(ii)
N-(2-Amino-2-oxoethyl)-3-[2-(methylamino)ethyl]-1H-indole-5-carboxamide hydrochloride compound with ethanol and water (10:10:1:3)

Dimethyl sulphate (0.26 g) was added to the product of Stage (i) (0.68 g) and potassium carbonate (0.5 g) in dimethylformamide with stirring. After 4 h the mixture was partitioned between ethyl acetate (150 ml) and water (150 ml), and the aqueous phase further extracted with ethyl acetate (50 ml). The combined organic extracts were washed with water (2×100 ml), dried ($Na_2SO_4$), and evaporated in vacuo to give the N-methyl derivative as an oil (0.38 g). [T.l.c. (A) Rf. 0.59].

A solution of the above product (0.32 g) in ethanol (30 ml) was hydrogenated over 10% palladium on charcoal (0.2 g) at room temperature and one atmosphere pressure for 6 h. (Hydrogen uptake 25 ml). The catalyst was filtered off, and washed with ethanol (3 ml), and ethereal hydrogen chloride (1 ml) was added. The mixture was diluted with ether (30 ml), and the resulting solid filtered off, washed with ether (2×20 ml), and dried in vacuo to give the *title compound* as a solid (0.13 g), m.p. 100°–110°.

Analysis found : C,53.1; H,6.2; N,17.1; $C_{14}H_{18}N_4O_2.HCl.0.1C_2H_6O.0.3H_2O$ requires : C,53.2; H,6.4; N,17.5%.

N.m.r. δ(DMSO-d6) includes 2.50 (3H, t, NH—C$\underline{H_3}$), 3.10 (4H, br s, C$\underline{H_2CH_2}$N), 3.80 (2H, d, C$\underline{H_2}$—NH—C=O), 8.70 (1H, br t, CON$\underline{H}$-CH$_2$) and 11.2 (1H, br s, indole —NH).

EXAMPLE 5

N-(3-Amino-3-oxopropyl)-3-(2-aminoethyl)-1H-indole-5-carboxamide, hydrochloride compound with ethanol and water (4:4:1:5).

(i) Phenylmethyl 2-[5-[[(3-amino-3-oxopropyl)amino]carbonyl]-1H-indol-3-yl]ethyl carbamate Intermediate 5 (5.0 g) and beta-alanine ethyl ester hydrochloride (3.0 g) were stirred together in dimethylformamide (25 ml) for 1.5 h. The mixture was partitioned between ethyl acetate (150 ml) and water (150 ml) and the aqueous phase was further extracted with ethyl acetate (100 ml). The combined organic extracts were washed with water (2×150 ml), dried (MgSO$_4$) and evaporated in vacuo to give an oil (5.0 g). This was chromatographed twice on silica eluting with 0.1% methanol in chloroform, and then ethyl acetate. The appropriate fractions were combined, and the solvent was removed in vacuo to give the ester as an oil (2.6 g) which was dissolved in methanolic ammonia (240 ml), and stirred at room temperature for 158 h. Solvent was removed in vacuo to give a solid (2.4 g) which was crystallised from aqueous ethanol to give the *title compound* as a microcrystalline solid (1.6 g), m.p. 169°–170°.

(ii) N-(3-Amino-3-oxopropyl)-3-(2-aminoethyl)-1H-indole-5-carboxamide hydrochloride compound with ethanol and water (4:4:1:5)

A solution of the product of Stage (i) (0.5 g) in ethanol (100 ml) was hydrogenated over 10% palladium on carbon (0.3 g) at room temperature and on atmosphere pressure for 18 h. The catalyst was filtered off, and washed with ethanol (2×15 ml). The combined filtrates were evaporated in vacuo to give a clear oil (0.4 g) which was dissolved in absolute ethanol (4 ml), and treated with ethereal hydrogen chloride (1 ml). The mixture was diluted with dry ether (50 ml) and stirred for 10 min. The resulting solid was filtered off, washed with ether, and dried in vacuo at 60° for 6 h to give the *title compound* as a hygroscopic solid (0.32 g).

Analysis found : C,50.1; H,6.5; N,15.8; $C_{14}H_{18}N_4O_2.HCl.0.25C_2H_6O.1.25H_2O$ requires : C,50.5; H,6.7; N,16.3%.

N.m.r. δ(DMSO-d6) includs 2.50 (2H, t, COC$\underline{H_2}$—CH$_2$), 3.15 (4H, br s, C$\underline{H_2CH_2}$—NH$_2$) 3.50 (2H, q, COCH$_2$-C$\underline{H_2}$) and 11.4 (1H, br s, indole —NH).

EXAMPLE 6

3-(2-Aminoethyl)-N-[2-oxo-2-(phenylamino)ethyl]-1H-indole-5-carboxamide hydrochloride hydrate (i) Phenylmethyl 2-[5-[[[2-oxo-2-(phenylamino)ethyl]amino]carbonyl]-1H-indol-3-yl]ethyl carbamate A solution of 3-[2-[[(Phenylmethoxy)carbonyl]amino]ethyl]-1H-indole-5-carboxylic acid (1.35 g) in dry tetrahydrofuran (27 ml), was stirred, under nitrogen and cooled to between −10° C and −5° C. Triethylamine (0.809 g) and methanesulphonyl chloride (0.5 g) were added nand stirring continued for 1 hr. 2-Amino-N-phenylacetamide (0.60 g) and 4-dimethylaminopyridine (0.097 g) in dry tetrahydrofuran (10 ml) were added and the resulting mixture was allowed to warm to room temperature. The reaction mixture was partitioned between hydrochloric acid (2N; 100 ml) and ethyl acetate (2×100 ml). The combined organic extracts were washed with sodium carbonate (2N; 100 ml), dried (MgSO$_4$) and evaporated in vacuo to give a foam (1.24 g). Flash chromatography (B) gave the product as a solid (0.69 g), which was crystallised from ethanol to give the *title compound* as a solid (0.35 g) m.p. 202.5°–203.5°.

(ii) 3-(2-Aminoethyl)-N-[2-oxo-2-(phenylamino)ethyl]-1H-indole-5-carboxamide hydrochloride hydrate A solution of the product of Stage (i), (0.30 g) in ethanol (50 ml) was added to pre-reduced 10% palladium oxide on charcoal (0.1 g; 50% aqueous paste) and ethanol (10 ml) and the resulting mixture hydrogenated at room temperature and pressure for 4 h. The catalyst was filtered off through 'hyflo' and the filtrate evaporated in vacuo to give an oil, which was dissolved in absolute alcohol (10 ml), and acidified with ethanolic hydrogen chloride. This solution was diluted with dry ether until the hydrochloride salt precipitated out. This was filtered off and dried in vacuo to give the *title compound* as a solid. (82.5 mg) m.p. 188°–191° C.

Analysis Found : C,58.3; H,5.7; N,13.7; $C_{19}H_{20}N_4O_2.HCl.H_2O$ requires : C,58.3; H,5.9; N,14.3%.

N.m.r. δ(DMSO-d6) includes 3.15 (4H, m. C$\underline{H_2CH_2}$—N),4.15 (2H, d, COC$\underline{H_2}$-N), 10.2 (1H, s, CON$\underline{H}$-Ph) and 11.3 (1H, br s, indole —NH).

EXAMPLE 7

N-(2-Amino-2-oxoethyl)-3-[2-(dimethylamino)ethyl]-1H-indole-5-carboxamide compound with ethanol and water (i) Methyl [[[3-(cyanomethyl)-1H-indol-5-yl]carbonyl]amino]acetate A stirred suspension of Intermediate 3 (1.973 g) in anhydrous tetrahydrofuran (100 ml) was treated with N,N-carbonyldiimidazole (1.74 g) and stirred at room temperature for 0.5 h. The suspension was heated under reflux for 0.75 h and then stirred at room temperature for 2 h. Triethylamine (1.36 ml), and glycine methyl ester hydrochloride (1.24 g) were added and the suspension stirred for 20 h at room temperature. A further portion of triethylamine (0.68 ml) and glycine methyl ester hydrochloride (0.62 g) was added and stirring continued at room temperature for another 5 h. The suspension was evaporated to dryness and the residue mixed thoroughly with 1N hydrochloric acid (100 ml) and extracted with ethyl acetate (8×200 ml). The combined organic extracts were washed with 8% sodium hydrogen carbonate (100 ml), dried (MgSO$_4$) and evaporated to dryness to afford a gum (1.05 g). This material was chromatographed on silica eluting with cyclohexane, cyclohexane/isopropyl acetate mixtures and isopropyl acetate.

Appropriate fractions were evaporated and triturated with dry ether to present the *title compound* as a powder (0.448 g) m.p. 138°–140°.

(ii)
N-(2-Amino-2-oxoethyl)-3-(cyanomethyl)-1H-indole-5-carboxamide

The product of Stage (i) (0.05 g) dissolved in methanolic ammonia (2 ml) was stirred overnight, further 2 ml portions of methanolic ammonia being added after 3.5 h and 5.5 h. The solution was evaporated to dryness and the residual solid triturated with anhydrous ether to present the product as a powder (0.036 g) m.p. 206°–209°.

Assay Found: C,60.4; H,4.8; N,21.4; C$_{13}$H$_{12}$N$_4$O$_2$.0.1CH$_3$OH requires C,60.6; H,4.8; N,21.6%.

(iii)
N-(2-Amino-2-oxoethyl)-3-[2-(dimethylamino)ethyl]-1H-indole-5-carboxamide

A suspension of the product of Stage (ii) (0.192 g) in 33% ethanolic dimethlamine (20 ml) was added to a slurry of pre-reduced 10% palladium oxide on carbon (0.3 g of a 50% paste with water) in ethanol (10 ml). The resultant mixture was hydrogenated at room temperature and atmospheric pressure for 24 h. Subsequent filtration (to remove the catalyst) and evaporation of the solvent left a gum (0.216 g), which was chromatographed on silica (C and D). Evaporation of the appropriate fractions afforded a colourless glass (0.197 g) which was triturated with anhydrous ether to present the *title compound* free base as a powder (0.144 g).

Water Assay Found: 0.95%. Theory 1.35%.
Analysis Found: C,60.7;H,7.7;N,18.1. C$_{15}$H$_{20}$N$_4$O$_2$.0.33EtOH.0.23H$_2$O requires C,61.1;H,7.35;N,18.2%.

N.m.r. δ(DMSO-d6) includes (2.20 (6H, s, N—Me$_2$), 2.58 (2H, t, CH$_2$—CH$_2$—NMe$_2$), 3.85 (2H, d, NH—CH$_2$—C=O), 8.55 (1H, t, CONH-CH$_2$) and 11.10 (1H, br s, indole —NH).

EXAMPLE 8

3-[2-(Dimethylamino)ethyl]-N-[2-oxo-2-[(phenylmethyl)amino]ethyl]-H-indole-5-carboxamide oxalate hydrate A suspension of Intermediate 4 (0.2 g) in dry pyridine (4 ml) at −5° was treated with thionyl chloride (0.064 ml) and stirred for 40 min. 2-Amino- N-benzylacetamide (0.1222 g) dissolved in dry pyridine (4 ml) was added (at −5°) and the solution allowed to stand at room temperature for 60 h. Evaporation of the pyridine afforded a gum (0.35 g) which was chromatographed on silica (C and D). Evaporation of the appropriate fractions gave the free base as a partially crystalline gum (0.084 g). A solution of the free base (0.063 g) in absolute alcohol (1 ml) was treated with a solution of oxalic acid (15 mg) in absolute alcohol (0.5 ml). The resultant suspension was diluted with absolute alcohol (1 ml) and the solid was filtered off and washed with absolute alcohol (2 ml) to give a powder (54 mg) m.p. 165°–170°.

Water Assay Found 1.31% H$_2$O. Theory (for ½H$_2$O)=1.26% Assay Found : C,60.5;H,5.7;N,11.8.

C$_{21}$H$_{26}$N$_4$O$_2$.C$_2$H$_2$O$_4$.½H$_2$O requires C,60.75;H,6.1;N,11.8%.

N.m.r δ(DMSO-d6) includes 2.80 (6H, s, N—Me$_2$), 3.17 (4H, AA'BB', CH$_2$CH$_2$-N), 3.97 (2H, d, NH—CH$_2$-C=O), 4.35 (2H, d, NH-CH$_2$-Ph), 8.70 (1H, t, CONH—CH$_2$—C=O) and 11.3 (1H, s, indole —NH).

The following examples illustrates a pharmaceutical formulation according to the invention containing N-(2-amino-2-oxoethyl)-3-[2-(methylamino) ethyl]-1H-indole-5-carboxamide hydrochloride as the active ingredient. Other compounds of the invention may be formulated in a similar manner.

Tablets for Oral Administration

|  | mg/tablet |
|---|---|
| Active Ingredient | 100 |
| Magnesium stearate BP | 1.0 |
| Anhydrous lactose | 99 |

The active ingredient is sieved and blended with the anhydrous lactose and magnesium stearate. The mix is then compressed into tablets using a Manesty F3 tablet machine fitted with 8.0 mm concave punches.

We claim:

1. A compound selected from compouns of the formula (I):

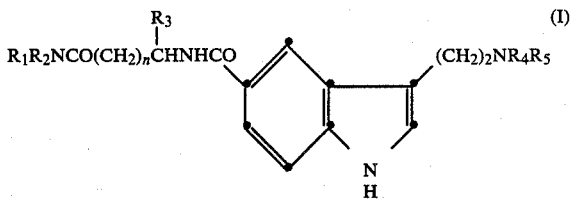

wherein
R$_1$ represents a hydrogen atom, a C$_{1-6}$ alkyl group, a C$_{3-7}$ cycloalkyl group, a phenyl group which may be unsubstituted or substituted by a C$_{1-3}$ alkoxy group or a phen(C$_{1-4}$) alkyl group in which the phenyl ring may be unsubstituted or substituted by a C$_{1-3}$ alkoxy group;

R$_2$ represents a hydrogen atom or a C$_{1-6}$ alkyl group;

R$_3$ represents a hydrogen atom or a C$_{1-3}$ alkyl group;

R$_4$ and R$_5$ which may be the same or different each represents a hydrogen atom, a C$_{1-3}$ alkyl group or 2-propenyl; and n represents zero or 1;
and physiologically acceptable salts and solvates thereof.

2. A compound according to claim 1, wherein, in the formula (I), R$_1$ represents a hydrogen atom, a C$_{1-6}$ alkyl group, a phenyl group or a phen(C$_{1-4}$)alkyl group.

3. A compound according to claim 1, wherein, in the formula (I), n represents zero.

4. A compound according to claim 1, wherein, in the formula (I), R$_2$ represents a hydrogen atom.

5. A compound according to claim 1, wherein, in the formula (I), R$_3$ represents a hydrogen atom.

6. A compound according to claim 1, wherein, in the formula (I), $R_4$ and $R_5$ which may be the same or different, each represents a hydrogen atom or a methyl group.

7. A compound according to claim 1, wherein, in the formula (I), $R_1$ represents a hydrogen atom or a phenylmethyl group, $R_2$ and $R_3$ each represents a hydrogen atom, $R_4$ represents a hydrogen atom or a methyl group, $R_5$ represents a methyl group and n is zero.

8. A compound according to claim 1, selected from
N-(2-amino-2-oxoethyl)-3-[2-(methylamino) ethyl-1H-indole-5-carboxamide;

N-(2-amino-2-oxoethyl)-3-[2-(dimethylamino) ethyl]-1H-indole-5-carboxamide;

and the physiologically acceptable salts and solvates thereof.

9. A pharmaceutical composition which comprises at least one compound selected from compounds of formula (I) as defined in claim 1 and physiologically acceptable salts and solvates thereof together with a pharmaceutically acceptable carrier or excipient therefor.

10. A method of treating a patient susceptible to or suffering from migraine which comprises administering to the patient a pharmaceutical composition as claimed in claim 9.

11. A method of treating a patient susceptible to or suffering from migraine which comprises administering to the patient an effective amount of a compound of formula (I) as defined in claim 1 or a physiologically acceptable salt or solvate thereof.

* * * * *